United States Patent [19]

Frickel et al.

[11] 4,315,939

[45] Feb. 16, 1982

[54] PIPERIDINE DERIVATIVES OF 4,5-DIALKYL-3-HYDROXY-PYRROLE-2-CARBOXYLIC ACID ESTERS, PHARMACEUTICAL FORMULATIONS CONTAINING THESE COMPOUNDS AND USE IN TREATING CARDIAC ARRHYTHMIAS

[75] Inventors: Fritz-Frieder Frickel, Deidesheim; Albrecht Franke, Wachenheim; Gerda Von Philipsborn, Weinheim; Claus D. Mueller, Viernheim; Dieter Lenke, Ludwigshafen, all of Fed. Rep. of Germany

[73] Assignee: BASF Aktiengesellschaft, Fed. Rep. of Germany

[21] Appl. No.: 194,441

[22] Filed: Oct. 6, 1980

[30] Foreign Application Priority Data

Oct. 13, 1979 [DE] Fed. Rep. of Germany ....... 2941597

[51] Int. Cl.$^3$ ................. A61K 31/445; C07D 401/04; C07D 401/12; C07D 401/14
[52] U.S. Cl. .................................. 424/267; 546/201; 546/208; 546/193; 546/194
[58] Field of Search ............... 546/208, 193, 194, 201; 424/267

[56] References Cited

FOREIGN PATENT DOCUMENTS 2630152 1/1978 Fed. Rep. of Germany ...... 546/208

*Primary Examiner*—Robert T. Bond
*Attorney, Agent, or Firm*—Keil & Witherspoon

[57] ABSTRACT

Substituted piperidinoalkyl ethers of 4,5-dialkyl-3-hydroxy-pyrrole-2-carboxylic acid esters and their physiologically tolerated addition salts with acids, processes for their preparation and pharmaceutical formulations which contain these compounds and are useful in the treatment of cardiac arrhythmias.

10 Claims, No Drawings

PIPERIDINE DERIVATIVES OF 4,5-DIALKYL-3-HYDROXY-PYRROLE-2-CARBOXYLIC ACID ESTERS, PHARMACEUTICAL FORMULATIONS CONTAINING THESE COMPOUNDS AND USE IN TREATING CARDIAC ARRHYTHMIAS

The present invention relates to substituted piperidinoalkyl ethers of 4,5-dialkyl-3-hydroxy-pyrrole-2-carboxylic acid esters and their physiologically tolerated addition salts with acids, to processes for their preparation and to pharmaceutical formulations which contain these compounds and are useful in the treatment of cardiac arrhythmias.

German Laid-Open Application DOS 2,630,152, Laid Open Jan. 19, 1978, describes derivatives of 1-phenoxy-propan-2-ol, containing a 4-(pyrid-2-yl)-piperidin-4-ol radical, which possess anti-arrhythmic properties. It is known to those skilled in the art that the prior art agents for counteracting cardiac arrhythmias are not always satisfactory and often have an insufficient therapeutic range.

We have found that compounds of the general formula I

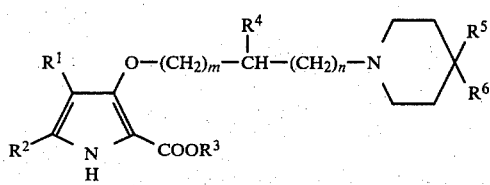

where $R^1$ and $R^2$ are identical or different and each is alkyl of 1 to 4 carbon atoms or aralkyl of 7 to 9 carbon atoms, or $R^1$ and $R^2$ together with the two carbon atoms by which they are linked form a 6-membered ring possessing 4 methylene groups and $R^3$ is alkyl of 1 to 6 carbon atoms, $R^4$ and $R^5$ are hydrogen or hydroxyl, $R^6$ is a 6-membered hetaryl or aryl radical which may be monosubstituted or disubstituted by halogen or monosubstituted by trifluoromethyl, and m and n are integers from 1 to 5 and the sum of $m+n$ does not exceed 6 and, if $R^4$ is hydrogen, m or n may also be 0, and their physiologically tolerated addition salts with acids exhibit valuable pharmacological properties.

Examples of alkyl and aralkyl radicals $R^1$ and $R^2$ are methyl, ethyl, propyl, butyl and benzyl.

If $R^1$ and $R^2$ together with the two carbon atoms form a ring, then such a ring is a 4,5,6,7-tetrahydroindole system.

Examples of $R^3$ are methyl, ethyl, propyl, i-propyl, butyl, pentyl and hexyl.

Suitable hetaryl and aryl radicals $R^6$ are pyridyl, especially β-pyridyl, and phenyl. In the case of radicals substituted by halogen, especially by fluorine, chlorine or bromine, or by $CF_3$, the substituents are, for example, 4-fluoro, 4-chloro, 3-fluoro, 3-chloro or 3-trifluoromethyl.

Suitable piperidinoalkyl radicals with which the 3-hydroxypyrrole is etherified include 3-piperidino-2-hydroxy-propoxy, 4-piperidino-butoxy, 2-piperidinoethoxy and 3-piperidino-propoxy, ie. m and n are 1 or m is 1 and n is 2 and, if $R^4$ is hydrogen, n may also be 0 when m is 1.

Particularly preferred compounds of the formula I are those in which $R^1$ is alkyl of 1 to 4 carbon atoms, especially methyl, $R^2$ is methyl, $R^3$ is methyl or ethyl, $R^4$ is hydrogen or hydroxyl, $R^5$ is hydroxyl and $R^6$ is α-pyridyl or phenyl, which is unsubstituted or substituted by fluorine, chlorine or bromine, m and n are 1 or 2 and, when $R^4$ is H, n may also be 0 when m is 1, and their physiologically tolerated addition salts with acids.

Within this group, compounds where m is 1 and n is 1 or 2 or, if $R^4$ is H, m is 1 and n is 0, are of particular importance.

Accordingly, examples of compounds according to the invention, of the general formula I, include: 3-[2-hydroxy-3-(4-phenyl-4-hydroxy-piperidino)-propoxy]-4,5-dimethylpyrrole-2-carboxylic acid ethyl ester, 3-[2-hydroxy-3-(4-phenyl-4-hydroxy-piperidino)-propoxy]-4,5-dimethylpyrrole-2-carboxylic acid methyl ester, 3-[2-hydroxy-3-(4-phenyl-4-hydroxy-piperidino)-propoxy]-4,5-dimethylpyrrole-2-carboxylic acid butyl ester, 3-[2-hydroxy-3-(4-phenyl-4-hydroxy-piperidino)-propoxy]-4-butyl-5-methylpyrrole-2-carboxylic acid ethyl ester, 3-[2-hydroxy-3-(4-phenyl-4-hydroxy-piperidino)-propoxy]-4-ethyl-5-methylpyrrole-2-carboxylic acid ethyl ester, 3-[2-hydroxy-3-(4-phenyl-4-hydroxy-piperidino)-propoxy]-4-ethyl-5-methylpyrrole-2-carboxylic acid methyl ester, 3-[2-hydroxy-3-(4-phenyl-4-hydroxy-piperidino)-propoxy]-4-benzyl-5-methylpyrrole-2-carboxylic acid ethyl ester, 3-[2-hydroxy-3-(4-(p-chlorophenyl)-4-hydroxy-piperidino)-propoxy]-4,5-dimethylpyrrole-2-carboxylic acid methyl ester, 3-[2-hydroxy-3-(4-(p-chlorophenyl)-4-hydroxy-piperidino)-propoxy]-4,5-dimethylpyrrole-2-carboxylic acid ethyl ester, 3-[2-hydroxy-3-(4-(p-fluorophenyl)-4-hydroxy-piperidino)-propoxy]-4,5-dimethylpyrrole-2-carboxylic acid methyl ester, 3-[2-hydroxy-3-(4-(p-fluorophenyl)-4-hydroxy-piperidino)-propoxy]-4,5-dimethylpyrrole-2-carboxylic acid ethyl ester, 3-[2-hydroxy-3-(4-(m-trifluorophenyl)-4-hydroxy-piperidino)-propoxy]-4,5-dimethylpyrrole-2carboxylic acid methyl ester, 3-[2-hydroxy-3-(4-(m-trifluorophenyl)-4-hydroxy-piperidino)-propoxy]-4,5-dimethylpyrrole-2-carboxylic acid ethyl ester, 3-[2-hydroxy-3-(4-phenyl-piperidino)-propoxy]-4,5-dimethylpyrrole-2-carboxylic acid methyl ester, 3-[2-hydroxy-3-(4-phenyl-piperidino)-propoxy]-4,5-dimethylpyrrole-2-carboxylic acid ethyl ester, 3-[2-hydroxy-3-(4-phenyl-piperidino)-propoxy]-4-ethyl-5-methyl-pyrrole-2-carboxylic acid ethyl ester, 3-[2-hydroxy-3-(4-phenyl-4-hydroxy-piperidino)-propoxy]-4,5,6,7-tetrahydro-2-indole-carboxylic acid methyl ester, 3-[2-hydroxy-3-(4-phenyl-4-hydroxy-piperidino)-propoxy]-4,5,6,7-tetrahydro-2-indole-carboxylic acid ethyl ester, 3-[2-hydroxy-3-(4-phenyl-4-hydroxy-piperidino)-propoxy]-4,5,6,7-tetrahydro-2-indole-carboxylic acid butyl ester, 3-[2-hydroxy-3-(4-(m-trifluorophenyl)-4-hydroxypiperidino)-propoxy]-4,5,6,7-tetrahydro-2-indole-carboxylic acid ethyl ester, 3-[2-hydroxy-3-(4-(p-fluorophenyl)-4-hydroxy-piperidino)-propoxy]-4,5,6,7-tetrahydro-2-indole-carboxylic acid ethyl ester, 3-[2-hydroxy-3-(4-(p-chlorophenyl)-4-hydroxy-piperidino)-propoxy]-4,5,6,7-tetrahydro-2-indole-carboxylic acid ethyl ester, 3-[2-phenyl-4-hydroxy-piperidino)-ethoxy]-4,5-dimethylpyrrole-2-carboxylic acid methyl ester, 3-[2-(4-phenyl-4-hydroxy-piperidino)-ethoxy]-4,5-dimethylpyrrole-2-carboxylic acid ethyl ester, 3-[2-hydroxy-3-(4-α-pyridyl-4-hydroxy-piperidino)-propoxy]-4,5- dimethylpyrrole-2-carboxylic acid ethyl ester, 3-[3(4-α-pyridyl-4-hydroxy-piperidino)-propoxy]-4,5-dimethyl-pyrrole-2-carboxylic acid ethyl ester, 3-[3-(4-α-pyridyl-4-hydroxy-piperidino)-propoxy]-4,5-dimethylpyrrole-2-carboxylic acid methyl ester, 3-[2-hydroxy-3-(4-α-pyridyl-4-hydroxy-piperidino)-propoxy]-4-ethyl-5-methyl-pyrrole-2-carboxylic acid methyl ester, 3-[2-hydroxy-3-(4-α-pyridyl-4-hydroxy-piperidino)-propoxy]-4-ethyl-5-methylpyrrole-2-carboxylic acid ethyl ester, 3-[2-(4-phenyl-4-hydroxy-piperidino)-ethyoxy]-4,5-dimethyl-pyrrole-2-carboxylic acid butyl ester, 3-[2-(4-phenyl-piperidino)-ethoxy]-4,5-dimethylpyrrole-2-carboxylic acid ethyl ester, 3-[3-(4-phenyl-4-hydroxypiperidino)-propoxy]-4,5-dimethylpyrrole-2-carboxylic acid methyl ester, 3-[3-(4-phenyl-4-hydroxy-piperidino)-propoxy]-4,5-dimethylpyrrole-2-carboxylic acid ethyl ester, 3-[3-(4-phenyl-4-hydroxy-piperidino)-propoxy]-4,5-dimethylpyrrole-2-carboxylic acid propyl ester, 3-[3-(4-phenyl-4-hydroxy-piperidino)-propoxy]-4,5-dimethylpyrrole-2-carboxylic acid butyl ester, 3-[4-(4-phenyl-4-hydroxy-piperidino)-butoxy]-4,5-dimethylpyrrole-2-carboxylic acid methyl ester, 3-[4-(4-phenyl-4-hydroxy-piperidino)-butoxy]-4,5-dimethylpyrrole-2-carboxylic acid ethyl ester, 3-[4-(4-phenyl-4-hydroxypiperidino)-butoxy]-4,5-dimethylpyrrole-2-carboxylic acid butyl ester, 3-[3-(4-phenyl-piperidino)-propoxy]-4,5-dimethylpyrrole-2-carboxylic acid ethyl ester, 3-[4-(4-phenyl-piperidino)-butoxy]-4,5-dimethylpyrrole-2-carboxylic acid ethyl ester, 3-[5-(4-phenyl-4-hydroxy-piperidino)-pentoxy]-4,5-dimethylpyrrole-2-carboxylic acid ethyl ester, 3-[5-(4-phenyl-4-hydroxy-piperidino)-pentoxy]-4,5-dimethylpyrrole-2-carboxylic acid methyl ester, 3-[3-(4-α-pyridyl-4-hydroxy-piperidino)-propoxy]-4-butyl-5-methyl-pyrrole-2-carboxylic acid ethyl ester, 3-[2-(4-phenyl-4-hydroxy-piperidino)-ethoxy]-4-butyl-5-methyl-pyrrole-2-carboxylic acid methyl ester, 3-[2-(4-phenyl-4-hydroxy-piperidino)-ethoxy]-4-butyl-5-methylpyrrole-2-carboxylic acid ethyl ester, 3-[2-(4-(p-fluorophenyl)-4-hydroxy-piperidino)-ethoxy]-4,5-dimethylpyrrole-2-carboxylic acid methyl ester, 3-[2-(4-(p-fluorophenyl)-4-hydroxy-piperidino)-ethoxy]-4,5-dimethyl-pyrrole-2-carboxylic acid ethyl ester, 3-[2-(4-(p-fluorophenyl)-4-hydroxy-piperidino)-ethoxy]-4-butyl-5-methyl-pyrrole-2-carboxylic acid methyl ester, 3-[2-(4-(p-fluorophenyl)-4-hydoxy-piperidino)-ethoxy]-4-butyl-5-methyl-pyrrole-2-carboxylic acid ethyl ester, 3-[2-hydroxy-3-(4-α-pyridyl-4-hydroxy-piperidino)-propoxy]-4-butyl-5-methyl-pyrrole-2-carboxylic acid ethyl ester, 3-]2-hydroxy-3(4-α-pyridyl-4-hydroxypiperidino)-propoxy]-4-butyl-5-methyl-pyrrole-2-carboxylic acid methyl ester, 3-[2-(4-α-pyridyl-4-hydroxypiperidino)-ethoxy]-4,5-dimethyl-pyrrole-2-carboxylic acid methyl ester, 3-[2(4-α-pyridyl-4-hydroxypiperidino)-ethoxy]-4,5-dimethyl-pyrrole-2-carboxylic acid ethyl ester, 3-[2-(4-α-pyridyl-4-hydroxy-piperidino)-ethoxy]-4-butyl-5-methyl-pyrrole-2-carboxylic acid methyl ester, 3-[2-(4-α-pyridyl-4-hydroxy-piperidino)-ethoxy]-4-butyl-5-methyl-pyrrole-2-carboxylic acid ethyl ester, 3-[3-(4-α-pyridyl-4-hydroxy-piperidino)-propoxy]-4-butyl-5-methyl-pyrrole-2-carboxylic acid methyl ester, 3-[4-(4-α-pyridyl-4-hydroxy-piperidino)-butoxy]-4,5-dimethyl-pyrrole-2-carboxylic acid methyl ester, 3-[4-(4-α-pyridyl-4-hydroxy-piperidino)-butoxy]-4-butyl-5-methyl-pyrrolecarboxylic acid methyl ester, 3-[4-(4-α-pyridyl-4-hydroxy-piperidino)-butoxy]-4,5-dimethyl-pyrrole-2-carboxylic acid ethyl ester, 3-[4-(4-α-pyridine-4-hydroxy-piperidino)-butoxy]-4-butyl-5-methyl-pyrrole-2-carboxylic acid ethyl ester, 3-[4-(4-(p-fluorophenyl)-4-hydroxy-piperidino)-butoxy]-4,5-dimethyl-pyrrole-2-carboxylic acid methyl ester, 3-[4-(4-(p-fluorophenyl)-4-hydroxy-piperidino)-butoxy]-4-butyl-5-methyl-pyrrole-2-carboxylic acid ethyl ester and 3-[4-(4-(p-fluorophenyl)-4-hydroxy-piperidino)-butoxy]-4,5-dimethyl-pyrrole-2-carboxylic acid ethyl ester.

The compounds according to the invention are obtained if a carboalkoxypyrrole of the formula II

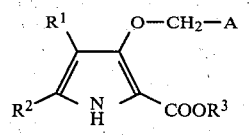

where $R^1$, $R^2$ and $R^3$ have the meanings given for formula I and A is

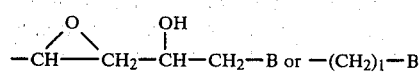

where B is a nucleofugic leaving group and l is an integer from 1 to 6, is reacted in a conventional manner with a piperidine derivative of the general formula III

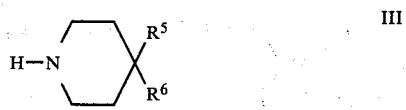

where $R^5$ and $R^6$ have the meanings given for formula I, advantageously in a solvent, and in the presence or absence of an acid acceptor, and, if desired, the resulting compound is converted to its addition salt with a physiologically tolerated acid.

The leaving group B is preferably halogen, especially chlorine, bromine or iodine. Further examples of suitable nucleofugic leaving groups are aromatic and aliphatic sulfonic acid radicals, eg. the p-toluenesulfonic acid, p-bromobenzenesulfonic acid or methanesulfonic acid radical.

The reaction is carried out at from 10° to 120° C., ie. at room temperature or above, advantageously at from 50° to 120° C. It may be carried out under atmospheric pressure or in a closed vessel under superatmospheric pressure, with or without heating to the stated temperature range.

The starting compounds may be reacted with one another direct, ie. without addition of a diluent or solvent. Advantageously, however, the reaction is carried out in the presence of an inert diluent or solvent, for example a lower alcohol of 1 to 4 carbon atoms, eg. methanol, ethanol or propanol, isopropanol or ethanol being preferred, a lower saturated dialkyl ether, dialkylglycol ether or cyclic ether, eg. diethyl ether, 1,2-dimethoxyethane, tetrahydrofuran or dioxane, an aromatic hydrocarbon, such as benzene or an alkylbenzene, eg. toluene or xylene, a saturated aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, or dimethylsulfoxide, or in the presence of water, or in mixtures of the above solvents.

Preferred solvents for the reaction of an epoxide of the formula (II), for example of 1-(2-carbomethoxy-4,5- dimethyl-pyrrol-3-oxy)-2,3-epoxypropane, 1-(2-carboethoxy-4,5-dimethyl-pyrrol-3-oxy)-2,3-epoxypropane, 1-(2-carboethoxy-4,5,6,7-tetrahydro-indol-3-oxy)-2,3-epoxypropane or 1-(2-carboethoxy-5-methyl-4-n-butyl-pyrrol-3-oxy)-2,3-epoxypropane, with a piperidine derivative of the general formula (III) are lower alcohols, especially isopropanol, and the reaction is preferably carried out at from 50° to 120° C., under atmospheric pressure.

For nucleophilic substitution reactions of a radical B in a compound of the formula (II) containing a radical -(CH$_2$)$_1$-B, for example 1-(2-carboethoxy-4,5-dimethyl-pyrrol-3-oxy)-3-chloro-propane, 1-(2-carbomethoxy-4,5-diemthyl-pyrrol-3oxy)-4-chloro-butane or 1-(2-carboethoxy-4,5,6,7-tetrahydro-2-indol-3-oxy)-3-chloro-propane, preferred solvents are lower aliphatic ketones, such as acetone, diethyl ketone, methyl isopropyl ketone and methyl isobutyl ketone, cyclic saturated ethers, especially tetrahydrofuran or dioxane, and dialkylformamides, eg. dimethylformamide, the reaction preferably being carried out at from 90° to 180° C., in the presence or absence of a catalytic amount of sodium iodide or potassium iodide.

A mixture of the epoxide with the halohydrin, such as may be formed in some cases when preparing the starting compounds of the formula II industrially, may also be used as the starting material for the above reactions.

In an advantageous embodiment of the nucleophilic substitution of the radical B by the piperidine derivative employed, the reaction is carried out in the presence of a base as the acid acceptor. Preferred bases are alkali metal hydroxides, carbonates, bicarbonates and alcoholates, and tertiary organic amines, such as pyridine or a trialkylamine, eg. trimethylamine or triethylamine. Amongst the alkali metal compounds, those of sodium or potassium are particularly suitable. The base is employed in stoichiometric amount or in slight excess. In some cases it may be advantageous to employ an excess of the piperidine derivative (III), used for the reaction, as the acid acceptor.

The time required to complete the reaction depends on the temperature and is in general from 2 to 15 hours. The product can be isolated in a conventional manner, for example by filtration, or by distilling the diluent or solvent from the reaction mixture. The compound obtained is purified in a conventional manner, for example by recrystallization from a solvent, by conversion to an addition compound with an acid or by column chromatography.

The starting compounds of the formula (II) may be obtained by alkylating the parent 3-hydroxypyrrole compound, for example 3-hydroxy-4,5-dimethyl-pyrrole-2-carboxylic acid ethyl ester, 4-butyl-3-hydroxy-5-methylpyrrole-2-carboxylic acid ethyl ester or 3-hydroxy-4,5,6,7-tetrahydroindole-2-carboxylic acid ethyl ester, with an epihalohydrin, an α, ω-dihalo-propan-2-ol or an α,ω-dihalopropane. Suitable epihalohydrins are epichlorohydrin, epibromohydrin and epiiodohydrin; suitable, α,ω-dihalo-propan-2-ols are, in particular, 1,3-dichloro-propan-2-ol and 1,3-dibromo-propan-2-ol, and suitable α,ω-dihalopropanes are, in particular, 1,3-chlorobromopropane, 1,3-dichloropropane, 1,3-dibromopropane, 1,2-chlorobromoethane and 1,4-chlorobromobutane.

The required hydroxypyrrolecarboxylic acid esters may be prepared as described in Liebigs Annalen, 1976, 384–386, or, for example in the case of 3-hydroxy-4,5-dimethyl-pyrrole-2-carboxylic acid methyl ester, by a process similar to that described in Liebigs Annalen, 736 (1970), 1–15.

The alkylation of the 2-carboalkoxy-3-hydroxypyrroles to prepare the starting compounds of the formula (II) is advantageously carried out at from 50° to 120° C. under atmospheric pressure or in a closed vessel under superatmospheric pressure. Advantageously, an inert diluent or solvent is used, for example a lower aliphatic ketone, eg. acetone, methyl ethyl ketone or methyl isobutyl ketone, a lower alcohol of 1 to 4 carbon atoms, eg. methanol, ethanol, propanol or butanol, a lower alkyl acetate, eg. methyl acetate, ethyl acetate or propyl acetate, a dialkylformamide, eg. dimethylformamide or diethylformamide, or dimethylsulfoxide, or an excess of the alkylating agent is employed as the diluent or solvent.

The reactions are preferably carried out in the presence of a base as the acid acceptor. Suitable bases are alkali metal carbonates, bicarbonates, hydroxides and alcoholates, especially of sodium and potassium, basic oxides, eg. aluminum oxide and calcium oxide, organic tertiary bases, eg. pyridine, or lower trialkylamines, eg. trimethylamine or triethylamine. The bases may be used in catalytic amounts, or in stoichiometric amounts or slight excess, based on alkylating agent employed.

Preferably, the 2-carboalkoxy-3-hydroxy-pyrroles are reacted with epibromohydrin, 1,3-dibromopropan-2-ol, 1,3-dibromopropane, 1,4-bromochlorobutane or 1,2-bromochloroethane in a lower aliphatic ketone, especially acetone or methyl isobutyl ketone, in the presence of not less than one equivalent of a base, especially potassium carbonate, based on alkylating agent, at from 50° to 80° C.

The starting compounds of the formula (II) containing, respectively, an epoxy group or a halohydrin structure may be converted into one another by simple acid-base reaction. For example, a 1-(2-carboethoxy-4,5-dimethyl-pyrrol-3-oxy)-2,3-epoxypropane may be converted, by means of the corresponding hydrogen halide, into 1-(2-carboethoxy-4,5-dimethylpyrrol-3-oxy)-3-halopropan-2-ol, in a diluent or solvent which may be one of those conventionally used or, preferably, an aliphatic or cyclic ether, eg. diethyl ether, tetrahydrofuran or dioxane, or a lower alcohol, eg. methanol, ethanol or propanol. Conversely, 1-(2-carboethoxy-4,5-dimethylpyrrol-3-oxy)-3-halo-propan-2-ol compounds, especially 1-(2-carboethoxy-4,5-dimethyl-pyrrol-3-oxy)-3-chloropropan-2-ol and 1-(2-carboethoxy-4,5-dimethyl-pyrrol-3-oxy)-3-bromopropan-2-ol, may be converted into 1-(2-carboethoxy-4,5-dimethyl-pyrrol-3-oxy)-2,3-epoxypropane by means of a base, eg. an alkali metal hydroxide, carbonate, bicarbonate, alcoholate or hydride, a tertiary organic amine, eg. pyridine, or piperidine, or a tertiary aliphatic amine, eg. trimethylamine or triethylamine.

These reactions may be carried out at room temperature or may be accelerated, or completed, by heating, for example at from 60° to 120° C.

The reaction may be carried out under atmospheric pressure or in a closed vessel under superatmospheric pressure, with or without heating. The starting materials for the reaction may be employed in the isolated form or may be produced in situ and be directly converted further, without prior isolation and purification.

The novel compounds of the formula I which have a hydroxyl group in the aliphatic side chain possess a chirality center and are obtained as racemates which can be separated into the optically active antipodes by conventional methods, for example by forming diastereomeric salts with optically active auxiliary acids, such as dibenzoyltartaric acid, camphor-10-sulfonic acid, ditoluyltartaric acid or 3-bromo-camphor-8-sulfonic acid.

A novel compound obtained may or may not be converted, by conventional methods, into an addition salt with a physiologically tolerated acid. Examples of conventional physiologically tolerated acids are, amongst inorganic acids, hydrochloric acid, hydrobromic acid, phosphoric acid and sulfuric acid, and, amongst organic acids, oxalic acid, maleic acid, fumaric acid, lactic acid, tartaric acid, malic acid, citric acid, salicylic acid, adipic acid and benzoic acid; other physiologically tolerated acids may be found in Fortschritte der Arzneimittelforschung, Birkhäuser-Verlag, Basel and Stuttgart, 10 (1966), 224–225, or J. Pharmaceutical Science, 66 (1977), 1–5.

The novel compounds, and their physiologically tolerated addition salts with acids, exhibit valuable pharmacological properties. They have a powerful anti-arrhythmic action and are therefore in particular suitable for the pharmacotherapy of cardiac arrhythmias.

To determine the anti-arrhythmic activity, the substances are administered orally to rats (Sprague Dawley, weight 200–250 g), 45 minutes before narcosis.

The animals are narcotized with sodium thiobutabarbital (100 mg/kg administered intraperitoneally). The arrhythmogenic substance used is aconitine, which is infused intravenously, at a rate of 0.005 mg/kg×min 60 minutes after the administration of the anti-arrhythmic agent. In untreated animals (N=52), arrhythmias manifest themselves in the electrocardiogram (ECG) after 2.74±0.07 min, and the occurrence of these can be delayed by the anti-arrhythmic agents, the delay being dependent on the dose.

The dose which lengthens the duration of infusion up to the occurrence of arrhythmias by 50%, namely the ED 50%, is determined from the linear relationships between log dose (mg/kg) of the test substance and the relative increase in the duration of aconitine infusion ($\Delta\%$).

For further characterization of the substances, the anti-arrhythmic effect of the maximum tolerated dose is determined from the decimal-geometric dose progression (factor $3\sqrt[3]{10}$) employed in the experiments. Furthermore, the dose at which toxic symptoms (changes in the initial ECG, cyanosis and cramps) occur is determined. The comparative substance used is the highly active prior art anti-arrhythmic agent Prajmalium (N-propylajmalin).

Table 1 shows that the compounds investigated for their effect on the aconitine-induced arrhythmia of rats are as active as Prajmalium (Examples 2, 11 and 13) or surpass the latter (Examples 6, 10 and 19). A further advantage is that on administration of the highest tolerated dose the effect produced is greater than in the case of Prajmalium. The maximum increase in the duration of aconitine infusion which Prajmalium produces is 174% whilst the compounds of Examples 1, 10, 11 and 19 produce a maximum increase of 324, 347, 308 and 302%.

The toxic doses of the substances according to the invention are higher than those of Prajmalium, with the exception of the compound of Example 6, which is of equal toxicity to Prajmalium. The increased toleration, coupled with a comparable or greater anti-arrhythmic activity, means that the compounds according to the invention have a greater therapeutic range, expressed as the quotient of the toxic dose and the anti-arrhythmically effective dose (ED 50%).

In the case of Prajmalium, toxic symptoms occur on administration of as little as 4.3 times the effective dose. Against this, the toxic doses of the novel substances of Example 6 and Example 10 are respectively 5.8 and 16 times greater than the effective doses.

TABLE 1

| | Anti-arrhythmic effect and toxicity in rats. Oral administration. | | | | | | |
|---|---|---|---|---|---|---|---|
| | Anti-arrhythmic effect on aconitine-induced arrhythmia | | | | | | |
| Substance | Effective dose, mg/kg | | Maximum effect[3] | | | Toxicity | |
| from Example | ED 50%[1] | R.A.[2] | Dose | $\Delta\%$[4] | R.M.E.[5] | Dose[6] | Q[7] |
| 1 | 7.80 | 0.64 | 46.4 | 324 | 1.86 | 100 | 13 |
| 2 | 6.23 | 0.80 | 21.5 | 170 | 0.98 | 46.4 | 7.5 |
| 6 | 3.68 | 1.36 | 10 | 152 | 0.87 | 21.5 | 5.8 |
| 7 | 13.5 | 0.37 | 46.4 | 307 | 1.76 | 100 | 7.4 |
| 10 | 2.99 | 1.67 | 21.5 | 347 | 1.99 | 46.4 | 16 |
| 11 | 5.54 | 0.90 | 21.5 | 308 | 1.77 | 46.4 | 8.4 |
| 13 | 5.93 | 0.84 | 21.5 | 149 | 0.86 | 46.4 | 7.8 |
| 19 | 3.38 | 1.48 | 21.5 | 302 | 1.74 | 46.4 | 14 |
| 21 | 9.85 | 0.51 | 46.4 | 173 | 0.99 | 100 | 10 |
| Prajmalium | 4.99 | 1.00 | 10 | 174 | 1.00 | 21.5 | 4.3 |

Footnotes to Table 1
[1]Dose which lengthens the duration of aconitine infusion by 50%
[2]R.A. = relative activity. Prajmalium = 1.00
[3]Effect of the maximum tolerated dose
[4]Lengthening of the duration of aconitin infusion, $\Delta\%$
[5]R.M.E. = relative maximum effect, Prajmalium = 1.00
[6]Dose whose administration produces the first toxic symptoms
[7]$Q = \frac{\text{toxic dose}}{\text{ED 50\%}}$ Accordingly, the present invention also relates to therapeutic agents or formulations which contain a compound of the formula I, or a physiologically tolerated acid addition salt thereof, as the active compound, together with conventional carriers and diluents, and to the use of the novel compounds in the pharmacotherapy of cardiac arrhythmias.

The novel compounds may be used in the conventional solid or liquid pharmaceutical forms for administration, such as tablets, capsules, powders, granules, dragees or solutions. These are prepared in a conventional manner. For this purpose, the active compounds may be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or nonaqueous vehicles, wetting agents, dispersants, emulsifiers and/or preservatives (cf. L. G. Goodman and A. Gilman, The Pharmacological Basis of Therapeutics). The formulations obtained normally contain from 0.001 to 99% by weight of the active compound.

The preferred formulations are those suitable for oral administration. Examples of these are tablets, film tablets, dragees, capsules, pills, powders, solutions, suspensions or forms which have a depot effect. Parenteral formulations, such as injection solutions, may also be used. Further examples of suitable formulations include suppositories.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetatephthalate or polyvinyl acetate. The tablets may also consist of a plurality of layers.

Accordingly, dragees may be prepared by coating cores, prepared in a similar manner to the tablets, with agents conventionally used in dragee coatings, for example collidone or shellac, gum arabic, talc, titanium dioxide or sugar. The dragee shell can also consist of several layers, in which the auxiliaries, mentioned above in connection with tablets, may be used.

Solutions or suspensions containing the novel active compounds may additionally contain flavorings, such as vanillin or orange extract. They may furthermore contain suspending agents, such as sodium carboxymethylcellulose, or preservatives, such as p-hydroxybenzoates. Capsules containing the active compounds may be prepared, for example, by mixing the latter with an inert carrier, such as lactose or sorbitol, and encapsulating the mixture in gelatin capsules. Suitable suppositories may be prepared, for example, by mixing the active compound with an appropriate carrier for this purpose, such as a neutral fat or polyethylene glycol or derivative thereof.

The dosage of the novel compounds depends on the age, condition and weight of the patient and on the route of administration. As a rule, the daily dose of active compound is from 5 to 100, preferably from 10 to 80, mg.

The Examples which follow illustrate the present invention.

I. Preparation of starting compounds

EXAMPLE I

3-Hydroxy-4,5,6,7-tetrahydroindole-2-carboxylic acid ethyl ester 294 g of 2-(ethoxycarbonylmethylamino)-cyclohexene-1-carboxylic acid ethyl ester in 400 ml of ethanol are added dropwise, under nitrogen, to a well-stirred solution of 35 g of sodium in 1.5 liters of ethanol. After the solution has boiled for three hours, it is cooled and 600 ml of water are then added, followed by 150 ml of concentrated hydrochloric acid. After the batch has stood for six hours at $-10°$ C., 142 g of 3-hydroxy-4,5,6,7-tetrahydroindole-2-carboxylic acid ethyl ester, of melting point 94°–95° C., are filtered off.

$C_{11}H_{15}NO_3$ (209.2): calculated: 63.2 C; 7.2 H; 6.7 N. found: 63.3 C; 7.4 H; 6.8 N

EXAMPLE II

3-Hydroxy-4,5-dimethyl-pyrrole-2-carboxylic acid ethyl ester

Using the method described in Example 1, 35 g of sodium in 1.5 liters of ethanol, and 264 g of 3-(ethoxycarbonylmethylamino)-2-methylcrotonic acid ethyl ester in 400 ml of ethanol give 165 g of 3-hydroxy-4,5-dimethyl-pyrrole-2-carboxylic acid ethyl ester, of melting point 111°–113° C.

$C_9H_{13}NO_3$ (183.1): calculated: 59.0 C; 7.1 H; 7.7 N. found: 59.2 C; 7.2 H; 7.5 N.

EXAMPLE III

3-Hydroxy-4,5-dimethyl-pyrrole-2-carboxylic acid methyl ester

Using the method described in Example 1, 5.7 g of sodium in 250 ml of methanol, and 40 g of 3-(methoxycarbonylmethylamino)-2-methylcrotonic acid methyl ester in 90 ml of methanol, give 28.1 g of 3-hydroxy-4,5-dimethyl-pyrrole-2-carboxylic acid methyl ester, of melting point 170°–172° C.

$C_8H_{11}NO_3$ (169.1): calculated: 56.8 C; 6.6 H; 8.3 N. found: 57.3 C; 6.6 H; 8.4 N.

EXAMPLE IV 3-(Methoxycarbonylmethylamino)-2-methylcrotonic acid methyl ester 72 g of a 30% strength solution of sodium methylate in methanol are added to a well-stirred suspension of 50 g of methyl glycinate hydrochloride in 20 ml of methanol and after 15 minutes 58 g of ethyl 2-methylacetoacetate are introduced. The reaction mixture is then refluxed for 8 hours, cooled to room temperature, diluted with 400 ml of ether and extracted by shaking twice with 300 ml of water at a time. The organic phase is dried over magnesium sulfate and concentrated under reduced pressure, and the crude product is subjected to fractional distillation. 47.6 g of 3-(methoxycarbonylamino)-2-methylcrotonic acid methyl ester, of boiling point 108°–110° C./0.2 mm Hg, are obtained.

$C_9H_{15}NO_4$(201.1): calculated: 53.7 C; 7.5 H; 7.0 N. found: 53.9 C; 7.5 H 6.9 N.

EXAMPLE V 1-(2-Carboethoxy-4,5-dimethyl-pyrrol-3-oxy)-2,3-epoxypropane 100 g of 2-carboethoxy-3-hydroxy-4,5-dimethylpyrrole, 150 g of epibromohydrin and 152 g of dry potassium carbonate in 500 ml of acetone are refluxed for 16 hours. When it has cooled, the entire reaction mixture is poured into 3 liters of ice water, the batch is extracted with ether and the combined extracts are washed with 2 N sodium hydroxide solution and water and dried over sodium sulfate. The evaporation residue which remains after distilling off the ether and the excess epibromohydrin is extracted with heptane. 122 g of 1-(2-carboethoxy-4,5-dimethyl-pyrrol-3-oxy)-2,3-epoxypropane, of melting point 70°–71° C., are obtained.

$C_{12}H_{17}NO_4$ (239.1): calculated: 60.3 C; 7.1 H; 5.9 N. found: 60.1 C; 7.0 H; 6.0 N.

EXAMPLE VI 1-(2-Carboethoxy-4,5,6,7-tetrahydroindol-3-oxy)-2,3-epoxypropane

Using the method described in Example V, 130 g of 3-hydroxy-4,5,6,7-tetrahydroindole-2-carboxylic acid ethyl ester, 170 g of epibromohydrin and 172 g of anhydrous potassium carbonate in 500 ml of acetone give 165 g of 1-(2-carboethoxy-4,5,6,7-tetrahydro-indol-3-oxy)-2,3-epoxypropane, of melting point 102°–104° C.

$C_{14}H_{19}NO_4$ (265.2): calculated: 63.4 C; 7.2 H; 5.3 N. found: 63.1 C; 7.2 H; 5.5 N.

EXAMPLE VII 1-(2-Carbomethoxy-4,5-dimethyl-pyrrol-3-oxy)-2,3-epoxypropane

Using the method described in Example V, 17 g of 2-carbomethoxy-3-hydro-4,5-dimethylpyrrole, 20 g of epibromohydrin and 28 g of dry potassium carbonate in 100 ml of acetone give 18.5 g of 1-(2-carbomethoxy-4,5-dimethyl-pyrrol-3-oxy)-2,3-epoxypropane, of melting point 85°–87° C.

$C_{11}H_{15}NO_4$ (225.1): calculated: 58.7 C; 6.7 H; 6.2 N. found: 58.5 C; 6.7 H; 6.5 N.

EXAMPLE VIII 1-(2-Carboethoxy-4-butyl-5-methyl-pyrrol-3-oxy)-2,3-epoxypropane Using the method described in Example V, 35 g of 2-carboethoxy-3-hydroxy-4-butyl-5-methyl-pyrrole, 32 g of epibromohydrin and 41 g of dry potassium carbonate in 100 ml of N,N-dimethylformamide, when heated at 50° C. for 8 hours, give 41 g of 1-(2-carboethoxy-4-butyl-5-methyl-pyrrol-3-oxy)-2,3-epoxypropane, of melting point 125°–127° C.

$C_{15}H_{23}NO_4$ (281.2): calculated: 64.1 C; 8.2 H; 5.0 N. found: 64.4 C; 8.1 H; 5.3 N.

EXAMPLE IX 1-(2-Carboethoxy-4-benzyl-5-methyl-pyrrol-3-oxy)-2,3-epoxypropane

Using the method described in Example V, 20 g of 2-carboethoxy-3-hydroxy-4-benzyl-5-methyl-pyrrole, 14 g of epibromohydrin and 20 g of dry potassium carbonate in 150 ml of methyl isobutyl ketone give 15 g of 1-(2-carboethoxy-4-benzyl-5-methyl-pyrrol-3-oxy)-2,3-epoxypropane as a pale yellow, very viscous oil.

$C_{18}H_{21}NO_4$ (315.2): calculated: 68.6 C; 6.7 H; 4.4 N. found: 68.2 C; 6.8 H; 4.7 N.

EXAMPLE X 1-(2-Carbomethoxy-4,5-dimethyl-pyrrol-3-oxy)-3-chloropropane 12 g of 3-hydroxy-4,5-dimethyl-pyrrole-2-carboxylic acid methyl ester, 13.8 g of 1,3-bromochloropropane and 13 g of anhydrous potassium carbonate in 50 ml of N,N-dimethylformamide are heated for 18 hours at 50° C. When the mixture has cooled, it is filtered and the filter residue is washed with acetone. The combined filtrates are partitioned between water and methylene chloride and the organic phase is repeatedly washed with water, dried over sodium sulfate and evaporated under reduced pressure. The residue which remains is recrystallized from methanol, in the presence of active charcoal. 9 g of 1-(2-carbomethoxy-4,5-dimethyl-pyrrol-3-oxy)-3-chloropropane, of melting point 117°–120° C., are obtained.

$C_{11}H_{16}NO_3Cl$ (245.5): calculated: 53.8 C; 6.6 H; 5.7 N; 14.4 Cl. found: 53.9 C; 6.7 H; 5.9 N; 14.7 Cl.

EXAMPLE XI 1-(2-Carbomethoxy-4,5-dimethylpyrrol-3-oxy)-2-chloroethane

Using the method described in Example X, 12 g of 3-hydroxy-4,5-dimethyl-pyrrole-3(?2)-carboxylic acid methyl ester, 14.2 g of 1,2-bromochloroethane and 13 g of anhydrous potassium carbonate give 9.5 g of 1-(2-carbomethoxy-4,5-dimethylpyrrol-3-oxy)-2-chloroethane, of melting point 122°–123° C.

$C_{10}H_{14}NO_3Cl$ (231.5): calculated: 51.8 C; 6.1 H; 6.1 N; 15.3 Cl. found: 51.3 C; 6.0 H; 6.0 N; 15.6 Cl.

EXAMPLE XII 1-(2-Carbomethoxy-4,5-dimethyl-pyrrol-3-oxy)-4-chlorobutane

Using the method described in Example X, 12 g of 3-hydroxy-4,5-dimethyl-pyrrole-2-carboxylic acid methyl ester, 15.5 g of 1,4-bromochlorobutane and 12.3 g of anhydrous potassium carbonate give 5.7 g of 1-(2-carbomethoxy-4,5-dimethyl-pyrrol-3-oxy)-4-chlorobutane, of melting point 74°–76° C.

$C_{12}H_{18}NO_3CL$ (259.5): calculated: 55.5 C; 7.0 H; 5.4 N; 13.7 Cl. found: 55.9 C; 6.8 H; 5.2 N; 13.2 Cl.

EXAMPLE XIII 1-(2-Carboethoxy-4,5-dimethyl-pyrrol-3-oxy)-4-chlorobutane

Using the method described in Example X, 18.3 g of 3-hydroxy-4,5-dimethyl-pyrrole-2-carboxylic acid ethyl ester, 22.3 g of 1,4-bromochlorobutane and 18 g of anhydrous potassium carbonate give 12.5 g of 1-(2-carboethoxy-4,5-dimethyl-pyrrol-3-oxy)-4-chlorobutane, of melting point 58°–60° C.

$C_{13}H_{20}NO_3Cl$ (273.5): calculated: 57.0 C; 7.4 H; 5.1 N; 13.0 Cl. found: 56.8 C; 7.2 H; 5.1 N; 12.6 Cl.

EXAMPLE XIV 1-(2-Carboethoxy-4,5-dimethyl-pyrrol-3-oxy)-3-chloropropane

Using the method described in Example X, 18.3 g of 3-hydroxy-4,5-dimethyl-pyrrole-2-carboxylic acid ethyl ester, 25 g of 1,3-bromochloropropane and 18 g of anhydrous potassium carbonate give 11.2 g of 1-(2-carboethoxy-4,5-dimethylpyrrol-3-oxy)-3-chloropropane, of melting point 60°–63° C.

$C_{12}H_{18}NO_3Cl$ (259.6): calculated: 55.5 C; 6.9 H; 5.4 N; 13.7 Cl. found: 55.2 C; 6.7 H; 5.1 N; 13.5 Cl.

EXAMPLE XV 1-(2-Carboethoxy-4,5-dimethyl-pyrrol-3-oxy)-2-chloroethane

Using the method described in Example X, 18.3 g of 3-hydroxy-4,5-dimethyl-pyrrole-2-carboxylic acid ethyl ester, 20.5 g of 1,2-bromochloroethane and 18 g of anhydrous potassium carbonate give 10 g of 1-(2-carboethoxy-4,5-dimethyl-pyrrol-3-oxy)-2-chloroethane, of melting point 81°–83° C.

$C_{11}H_{16}NO_3Cl$ (245.6): calculated: 53.8 C; 6.5 H; 5.7 N; 14.4 Cl. found: 54.2 C; 6.5 H; 5.9 N; 14.7 Cl.

EXAMPLE XVI 4.0 g of 1-(2-carboxyethoxy-4,5-dimethyl-pyrrol-3-oxy)-2,3-epoxypropane are dissolved in a mixture of 20 ml of ethanol and 15 ml of an about 4 N solution of hydrogen chloride in ether. After the mixture has stood for one day, the volatile constituents are distilled off and the evaporation residue is chromatographed over silica gel, using methylene chloride. 2.7 g of 1-(2-carboethoxy-4,5-dimethyl-pyrrol-3-oxy)-3-chloro-propan-2-ol, which is pure according to NMR spectroscopy, are obtained.

$^1$H-NMR spectrum (CDCl$_3$, with TMS as the internal standard):

$\tau$=1.4 (broad s, 1H); 5.5 (s, OH); 5.7 (g 2H, J=4.5 Hz); 5.9 (m, 3H); 6.4 (m, 2H); 7.88 (s, 3H); 8.1 (s, 3H); 8.7 (t, 3H, J=4.5 Hz).

II. Compounds according to the invention

EXAMPLE 1

24 g of 1-(2-carboethoxy-4,5-dimethyl-pyrrol-3-oxy)-2,3-epoxypropane and 18 g of 4-(2-pyridyl)-piperidin-4-ol in 200 ml of ethanol are refluxed for 4 hours. The residue which remains after distilling off the ethanol is dissolved in a small amount of methanol and a solution of hydrogen chloride in ether is added dropwise. The crystals which have precipitated are filtered off, waashed with ether and dried. 29 g of 3-[2-hydroxy-3-(4-α-pyridyl-4-hydroxy-piperidino)-propoxy]-4,5-dimethyl-pyrrole-2-carboxylic acid ethyl ester dihydrochloride, of melting point 227°–229° C., are obtained.

C$_{22}$H$_{33}$N$_3$O$_5$Cl$_2$ (490.1): calculated: 53.8 C; 6.7 H; 8.6 N; 14.5 Cl. found: 53.5 C; 6.7 H; 8.5 N; 14.3 Cl.

EXAMPLE 2

55 g of 1-(2-carboethoxy-4,5-dimethyl-pyrrol-3-oxy)-2,3-epoxypropane and 41 g of 4-hydroxy-4-phenyl-piperidine in 600 ml of ethanol are refluxed for 8 hours. The residue which remains after distilling off the ethanol is dissolved in a small amount of methanol and a solution of hydrogen chloride in ether is added dropwise. The crystals which have precipitated are filtered off, washed with ether and dried. 81 g of 3-[2-hydroxy-3-(4-phenyl-4-hydroxy-piperidino)-propoxy]-4,5-dimethyl-pyrrole-2-carboxylic acid ethyl ester hydrochloride, of melting point 211°–212° C., are obtained.

C$_{23}$H$_{33}$N$_2$O$_5$Cl (454.0): calculated: 61.0 C; 7.3 H; 17.7 O; 6.2 N; 7.8 Cl. found: 61.2 C; 7.1 H; 17.9 O; 5.9 N.

EXAMPLE 3

Using the method described in Example 1, 4.0 g of 1-(2-carboethoxy-4,5,6,7-tetrahydro-indol-3-oxy)-2,3-epoxypropane and 2.8 g of 4-hydroxy-4-phenyl-piperidine in 50 ml of ethanol give 5.7 g of 3-[2-hydroxy-3-(4-phenyl-4-hydroxy-piperidino)-propoxy]-4,5,6,7-tetrahydroindole-2-carboxylic acid ethyl ester hydrochloride, of melting point 170°–173° C.

C$_{25}$H$_{35}$N$_2$O$_5$Cl (478.7): calculated: 62.7 C; 7.4 H; 16.7 O; 5.8 N. found: 62.7 C; 7.6 H; 17.1 O; 5.5 N.

EXAMPLE 4

50 g of 1-(2-carboethoxy-4,5-dimethyl-pyrrol-3-oxy)-3-chloropropane, 35 g of 4-hydroxy-4-phenyl-piperidine and 50 g of sodium carbonate in 300 ml of N,N-dimethylformamide are heated for 20 hours at 100° C. When the mixture has cooled, it is partitioned between water and methylene chloride, the organic phase is evaporated under reduced pressure, the residue which remains in dissolved in a small amount of methanol, and a solution of hydrogen chloride in ether is added dropwise. The crystals which precipitate are filtered off, washed with ether and dried. 56 g of 3-[3-(4-phenyl-4-hydroxy-piperidino)-propoxy]-4,5-dimethylpyrrole-2-carboxylic acid ethyl ester hydrochloride, of melting point 165°–169° C., are obtained.

C$_{23}$H$_{33}$N$_2$O$_4$Cl (437.5): calculated: 63.1 C; 7.5 H; 6.4 N. found: 63.2 C; 7.7 H; 6.7 N.

EXAMPLE 5

6.0 g of 1-(2-carboethoxy-4,5-dimethyl-pyrrol-3-oxy)-3-chloro-propan-2-ol and 3.5 g of 4-hydroxy-4-phenyl-piperidine in 150 ml of dioxane are heated for 15 hours in an autoclave at 120° C. The volatile constituents are then distilled off under reduced pressure, and the very viscous crude product is partitioned between ether and 2 N sulfuric acid. The aqueous phase is cautiously rendered alkaline with 4 N sodium hydroxide solution and is then extracted with ether. The ether phase is dried over magnesium sulfate, the solvent is removed and the residue which remains is, as described in Example 2, dissolved in a small amount of methanol and treated with a solution of hydrogen chloride in ether, to give 3.2 g of 3-[2-hydroxy-3-(4-phenyl-4-hydroxy-piperidino)-propoxy]-4,5-dimethylpyrrole-2-carboxylic acid ethyl ester hydrochloride, of melting point 210°–212° C.

The compounds shown in Table 2 are obtained from the corresponding glycidyl ethers and 4-hydroxy-4-phenyl-piperidines using the method described in Example 2, or from the corresponding 1-(2-carboethoxy-4,5-dimethyl-pyrrol-3-oxy)-chloroalkanes and 4-hydroxy-4-phenyl-piperidines, using the method described in Example 4.

TABLE 2

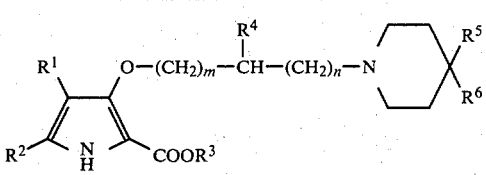

| Example Number | R$^1$ | R$^2$ | R$^3$ | R$^4$ | R$^5$ | R$^6$ | m | n | Salt form | M.p. °C. |
|---|---|---|---|---|---|---|---|---|---|---|
| 6 | CH$_3$ | CH$_3$ | CH$_3$ | H | OH |  | 1 | 1 | — | 140–141 |

TABLE 2-continued $$\underset{R^2\phantom{XX}\underset{H}{N}\phantom{XX}COOR^3}{R^1\phantom{XXX}O-(CH_2)_m-\overset{R^4}{\underset{|}{CH}}-(CH_2)_n-N\underset{R^6}{\overset{R^5}{\diagup}}}$$

| | $R^1$ | $R^2$ | $R^3$ | $R^4$ | $R^5$ | $R^6$ | m | n | | m.p. |
|---|---|---|---|---|---|---|---|---|---|---|
| 7 | CH₃ | CH₃ | CH₃ | OH | OH | 2-pyridyl | 1 | 1 | 2 HCl | 220–221 |
| 8 | CH₃ | CH₃ | CH₃ | H | OH | phenyl | 1 | 0 | — | 122–123 |
| 9 | CH₃ | CH₃ | C₂H₅ | H | OH | phenyl | 1 | 2 | HCl | 184–185 |
| 10 | CH₃ | CH₃ | C₂H₅ | H | OH | phenyl | 1 | 0 | HCl | 227–228 |
| 11 | CH₃ | CH₃ | CH₃ | H | OH | phenyl | 1 | 2 | — | 136–137 |
| 12 | CH₃ | CH₃ | C₂H₅ | OH | H | phenyl | 1 | 1 | HCl | 244–245 |
| 13 | CH₃ | CH₃ | C₂H₅ | OH | OH | 4-F-phenyl | 1 | 1 | HCl | 216–218 |
| 14 | CH₃ | CH₃ | C₂H₅ | OH | OH | 3-CF₃-phenyl | 1 | 1 | HCl | 152–154 |
| 15 | —(CH₂)₄— | C₂H₅ | OH | OH | 3-CF₃-phenyl | 1 | 1 | HCl | 196–198 |
| 17 | CH₃ | CH₃ | C₂H₅ | OH | OH | 3-Cl-phenyl | 1 | 1 | ½ HOOC-CH=CH-COOH | 214–216 |
| 18 | —(CH₂)₄— | C₂H₅ | OH | OH | 4-F-phenyl | 1 | 1 | — | 171–173 |
| 19 | CH₃ | CH₃ | CH₃ | OH | OH | phenyl | 1 | 1 | HCl | 216–217 |
| 20 | CH₂-phenyl | CH₃ | C₂H₅ | OH | OH | phenyl | 1 | 1 | (COOH)₂ H₂O | 110–112 |
| 21 | n-C₄H₉ | CH₃ | C₂H₅ | OH | OH | phenyl | 1 | 1 | (COOH)₂ | 124–126 |

| Example | Analyses | Name |
|---|---|---|
| 6 | calc.: 68.4 C 7.8 H 7.3 N<br>found: 68.1 C 7.7 H 7.4 N | 3-[3-(4-phenyl-4-hydroxy-piperidino)-propoxy]-4,5-dimethylpyrrole-2-carboxylic acid methyl ester |
| 7 | calc.: 53.0 C 6.6 H 8.8 N 14.9 Cl<br>found: 52.9 C 6.6 H 8.7 N 15.2 Cl | 3-[2-hydroxy-3-(4-α-pyridyl-4-hydroxy-piperidino)-propoxy]-4,5-dimethylpyrrole-2-carboxylic acid methyl ester |
| 8 | calc.: 67.7 C 7.6 H 7.5 N | 3-[2-(4-phenyl-4-hydroxy-piperidino)-ethoxy]-4,5-dimethylpyrrole-2- |

TABLE 2-continued $$R^2 \underset{\underset{H}{N}}{\overset{R^1}{\diagdown}} \overset{O-(CH_2)_m-\overset{R^4}{\underset{|}{CH}}-(CH_2)_n-N\diagup\diagdown\overset{R^5}{\underset{R^6}{\diagdown\diagup}}}{COOR^3}$$

| | | |
|---|---|---|
| 9 | found: 67.5 C 7.5 H 7.7 N<br>calc.: 63.9 C 7.8 H 6.2 N 7.9 Cl | carboxylic acid methyl ester<br>3-[4-(4-phenyl-4-hydroxy-piperidino)-butoxy]-4,5-dimethylpyrrole-2-carboxylic acid ethyl ester |
| 10 | found: 63.6 C 7.6 H 6.2 N 7.8 Cl<br>calc.: 62.5 C 7.4 H 6.6 N 8.4 Cl | 3-[2-(4-phenyl-4-hydroxy-piperidino)-ethoxy]-4,5-dimethylpyrrole-2-carboxylic acid ethyl ester |
| 11 | found: 62.1 C 7.2 H 6.6 N 8.3 Cl<br>calc.: 69.0 C 8.1 H 7.0 N | 3-[4-(4-phenyl-4-hydroxy-piperidino)-butoxy]-4,5-dimethylpyrrole-2-carboxylic acid methyl ester |
| 12 | found: 68.7 C 7.7 H 7.0 N<br>calc.: 63.2 C 7.6 H 14.7 O 6.4 N 8.1 Cl | 3-[2-hydroxy-3-(4-phenyl-piperidino)-propoxy]-4,5-dimethylpyrrole-2-carboxylic acid ethyl ester |
| 13 | found: 62.5 C 7.6 H 14.7 O 6.4 N 8.3 Cl<br>calc.: 58.7 C 6.9 H 6.0 N 4.0 F 7.3 Cl | 3-[2-hydroxy-3-(4-(p-fluorophenyl)-4-hydroxy-piperidino)-propoxy]-4,5-dimethylpyrrole-2-carboxylic acid ethyl ester |
| 14 | found: 58.2 C 6.6 H 5.6 N 3.8 F 7.7 Cl<br>calc.: 55.3 C 6.1 H 5.4 N 10.9 F 6.8 Cl | 3-[2-hydroxy-3-(4-(m-trifluoromethylphenyl)-4-hydroxy-piperidino)-propoxy]-4,5-dimethylpyrrole-2-carboxylic acid ethyl ester |
| 15 | found: 55.9 C 6.1 H 5.5 N 11.1 F 7.2 Cl<br>calc.: 57.1 C 6.3 H 5.1 N 10.4 F 6.4 Cl | 3-[2-hydroxy-3-(4-(m-trifluoromethylphenyl)-4-hydroxy-piperidino)-propoxy]-4,5,6,7-tetrahydroindole-2-carboxylic acid ethyl ester |
| 16 | found: 57.0 C 6.1 H 5.0 N 10.3 F 6.4 Cl<br>calc.: 58.5 C 6.7 H 5.5 N 13.8 Cl | 3-[2-hydroxy-3-(4-(p-chlorophenyl)-4 hydroxy-piperidino)-propoxy]-4,5,6,7-tetrahydroindole-2-carboxylic acid ethyl ester |
| 17 | found: 58.1 C 6.5 H 5.2 N 13.8 Cl<br>calc.: 59.0 C 6.5 H 5.5 N 7.0 Cl | 3-[2-hydroxy-3-(4-(p-chlorophenyl)-4-hydroxy-piperidino)-propoxy]-4,5-dimethylpyrrole-2-carboxylic acid ethyl ester |
| 18 | found: 58.5 C 6.3 H 5.5 N 6.9 Cl<br>calc.: 60.4 C 6.9 H 5.6 N 7.5 Cl | 3-[2-hydroxy-3-(4-(p-fluorophenyl)-4-hydroxy-piperidino)-propoxy]-4,5,67-tetrahydroindole-2-carboxylic acid ethyl ester |
| 19 | found: 59.9 C 6.8 H 5.5 N 7.5 Cl<br>calc.: 60.2 C 7.1 H 6.4 N 8.1 Cl | 3-[2-hydroxy-3-(4-phenyl-4-hydroxy-piperidino)-propoxy]-4,5-dimethyl-pyrrole-2-carboxylic acid methyl ester |
| 20 | found: 60.0 C 6.9 H 6.5 N 8.2 Cl<br>calc.: 61.9 C 6.7 H 4.7 N | 3-[2-hydroxy-3-(4-phenyl-4-hydroxy-piperidino)-propoxy]-4-benzyl-5-methyl-pyrrole-2-carboxylic acid ethyl ester |
| 21 | found: 61.5 C 6.5 H 4.7 N<br>calc.: 61.3 C 7.4 H 5.1 N | 3-[2-hydroxy-3-(4-phenyl-4-hydroxy-piperidino)-propoxy]-4-n-butyl-5-methyl-pyrrole-2-carboxylic acid ethyl ester |
| | found: 61.6 C 7.2 H 5.3 N | |

III. Examples of formulations

1. Tablets:

| | |
|---|---|
| (a) An active compound of the formula I | 5 mg |
| Lactose | 200 mg |
| Methylcellulose | 15 mg |
| Corn starch | 50 mg |
| Talc | 11 mg |
| Magnesium stearate | 4 mg |
| (b) An active compound of the formula I | 20 mg |
| Lactose | 178 mg |
| Avicel | 80 mg |
| Polywachs 6000 | 20 mg |
| Magnesium stearate | 2 mg |
| (c) An active compound of the formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |

The active compound is moistened with a 10% strength aqueous solution of the polyvinylpyrrolidone, forced through a sieve of 1.0 mm mesh width and dried at 50° C. The granules obtained are mixed with polyethylene glycol (mean molecular weight 4,000), hydroxypropylmethylcellulose, talc and magnesium stearate and the mixture is molded to form tablets each weighing 280 mg.

2. Example of degrees

| | |
|---|---|
| An active compound of the formula I | 60 mg |
| Lactose | 90 mg |
| Corn starch | 60 mg |
| Polyvinylpyrrolidone | 6 mg |

| 2. Example of degrees | |
|---|---|
| Magnesium stearate | 1 mg |

The mixture of the active compound, lactose, corn starch and an 8% strength aqueous solution of the polyvinylpyrrolidone is granulated by forcing through a 1.5 mm sieve and the granules are dried at 50° C. and then forced through a 1.0 mm sieve. The granules from this operation are mixed with magnesium stearate and the mixture is molded to form dragee cores. The cores obtained are provided, in a conventional manner, with a coating which essentially consists of sugar and talc.

| 3. Capsule formulation | |
|---|---|
| An active compound of the formula I | 5 mg |
| Magnesium stearate | 2.0 mg |
| Lactose | 19.3 mg |
| 4. Injection solution | |
| An active compound of the formula I | 10 mg |
| Sodium chloride | 9 mg |
| Distilled water, q.s. to make up to 1.0 ml | |

We claim:
1. A compound of the formula I

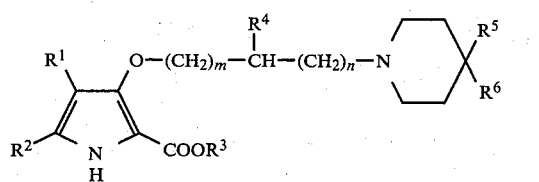

where
  $R^1$ and $R^2$ are identical or different and each is alkyl of 1 to 4 carbon atoms or aralkyl of 7 to 9 carbon atoms, or $R^1$ and $R^2$ together with the two carbon atoms by which they are linked form a 6-membered ring possessing 4 methylene groups and
  $R^3$ is alkyl of 1 to 6 carbon atoms,
  $R^4$ and $R^5$ are hydrogen or hydroxyl,
  $R^6$ is a pyridyl or phenyl radical which may be monosubstituted or disubstituted by halogen or monosubstituted by trifluoromethyl, and
  m and n are integers from 1 to 5 and the sum of m+n does not exceed 6 and, if $R^4$ is hydrogen, m or n may also be 0,
and its physiologically tolerated addition salts with acids.

2. A compound of the formula I as claimed in claim 1, in which $R^1$ is alkyl of 1 to 4 carbon atoms, $R^2$ is methyl, $R^3$ is methyl or ethyl, $R^4$ is hydrogen or hydroxyl, $R^5$ is hydroxyl and $R^6$ is α-pyridyl or phenyl, which is unsubstituted or substituted by fluorine, chlorine or bromine, m and n are 1 or 2 and, when $R^4$ is hydrogen, n may also be 0 when m is 1, and its physiologically tolerated addition salts with acids.

3. 3-[2-Hydroxy-3-(4-α-pyridyl-4-hydroxy-piperidino)-propoxy]-4,5-dimethyl-pyrrole-2-carboxylic acid ethyl ester and its physiologically tolerated addition salts with acids.

4. 3-[2-Hydroxy-3-(4-phenyl-4-hydroxy-piperidino)-propoxy]-4,5-dimethylpyrrole-2-carboxylic acid ethyl ester and its physiologically tolerated addition salts with acids.

5. 3-[2-Hydroxy-3-(4-α-pyridyl-4-hydroxy-piperidino)-propoxy]-4,5-dimethylpyrrole-2-carboxylic acid methyl ester and its physiologically tolerated addition salts with acids.

6. 3-[2-(4-Phenyl-4-hydroxy-piperidino)-ethoxy]-4,5-dimethylpyrrole-2-carboxylic acid ethyl ester and its physiologically tolerated addition salts with acids.

7. 3-[4-(4-Phenyl-4-hydroxy-piperidino)-butoxy]-4,5-dimethylpyrrole-2-carboxylic acid methyl ester and its physiologically tolerated addition salts with acids.

8. 3-[2-Hydroxy-3-(4-phenyl-4-hydroxy-piperidino)-propoxy]-4,5-dimethylpyrrole-2-carboxylic acid methyl ester and its physiologically tolerated addition salts with acids.

9. A therapeutic agent for treating cardiac arrhythmias which contains an effective amount of a compound of the formula I as claimed in claim 1, or a physiologically tolerated acid addition salt thereof, as the active compound, together with conventional carriers and diluents.

10. A process for treating cardiac arrhythmias which comprises: orally administering to the patient an effective daily dose of the therapeutic agent of claim 9.

* * * * *